(12) United States Patent
Kugelmann et al.

(10) Patent No.: US 9,132,220 B2
(45) Date of Patent: Sep. 15, 2015

(54) MULTICHAMBER CONTAINER FOR PREPARING MEDICINAL SOLUTIONS

(75) Inventors: Franz Kugelmann, St. Wendel/Bliesen, DE (US); Joern Hoermann, Heusweiler (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 546 days.

(21) Appl. No.: 13/446,514

(22) Filed: Apr. 13, 2012

(65) Prior Publication Data
US 2012/0288572 A1    Nov. 15, 2012

Related U.S. Application Data

(60) Provisional application No. 61/475,405, filed on Apr. 14, 2011.

(30) Foreign Application Priority Data

Apr. 14, 2011   (DE) .......................... 10 2011 017 048

(51) Int. Cl.
*A61J 1/20* (2006.01)
*A61M 1/16* (2006.01)
*A61J 1/10* (2006.01)

(52) U.S. Cl.
CPC ............ *A61M 1/1656* (2013.01); *A61J 1/2024* (2015.05); *A61J 1/2093* (2013.01); *A61M 1/167* (2014.02); *A61M 1/1666* (2014.02); *A61J 1/10* (2013.01)

(58) Field of Classification Search
CPC .............. A61B 5/00; A61F 2/04; A61F 9/00; A61H 35/00; A61J 1/20; A61M 1/00; A61M 5/00; A61M 27/00
USPC .......... 604/403, 408–410, 415, 416; 206/438, 206/531, 532, 538–540; 220/4.01, 220/4.21–4.24, 4.26, 4.27, 62.11, 62.22, 220/500, 507, 520, 524, 525, 553–555
See application file for complete search history.

(56) References Cited

U.S. PATENT DOCUMENTS

| 4,386,634 A | 6/1983 | Stasz et al. |
| 6,082,585 A | 7/2000 | Mader et al. |
| 7,544,301 B2 | 6/2009 | Shah et al. |
| 2005/0031509 A1 | 2/2005 | D'Ayot et al. |

(Continued)

FOREIGN PATENT DOCUMENTS

| DE | 196 05 357 | 8/1997 |
| DE | 197 51 489 | 5/1999 |

(Continued)

*Primary Examiner* — Melanie Hand
(74) *Attorney, Agent, or Firm* — Jacobson Holman, PLLC

(57) ABSTRACT

A multichamber container and a method of preparing medical fluids having concentrates which make a contribution toward the electrical conductivity of the solution and are additionally prepared from concentrates which do not make a contribution toward the electrical conductivity of the solution. The multichamber container is configured by dividing solution components into multiple chambers, so that following the dissolving due to breaking open of the first chamber border of a solution component, which makes a contribution toward the electrical conductivity of the medicinal solution, another chamber border of another solution component which does not make any contribution toward the electrical conductivity of the solution is broken open.

20 Claims, 7 Drawing Sheets

(56) References Cited

U.S. PATENT DOCUMENTS

| | | | |
|---|---|---|---|
| 2008/0017543 A1* | 1/2008 | Pahlberg et al. | 206/532 |
| 2009/0166363 A1 | 7/2009 | Balteau | |
| 2009/0274774 A1* | 11/2009 | Shah et al. | 424/680 |
| 2010/0280485 A1 | 11/2010 | Choi et al. | |

FOREIGN PATENT DOCUMENTS

| | | |
|---|---|---|
| DE | 198 09 945 | 9/1999 |
| EP | 0 846 470 | 6/1998 |
| EP | 1 059 083 | 12/2000 |
| EP | 1 458 433 | 7/2003 |
| EP | 1 621 177 | 2/2006 |
| EP | 1 773 277 | 2/2006 |
| FR | 2 766 797 | 2/1999 |
| WO | WO 00/57833 | 10/2000 |
| WO | WO 2007/144427 | 12/2007 |
| WO | WO 2008/069731 | 6/2008 |
| WO | WO 2009/086300 | 7/2009 |

\* cited by examiner

MULTICHAMBER CONTAINER FOR PREPARING MEDICINAL SOLUTIONS

CROSS-REFERENCE TO RELATED APPLICATIONS

This application is claiming benefit of U.S. provisional application No. 61/475,405, filed Apr. 14, 2011, which claims the priority of German number 10 2011 017 048.0, filed Apr. 14, 2011, hereby incorporated by reference.

BACKGROUND OF THE INVENTION

1. Field of Invention

The subject matter of the invention is a multichamber bag for holding concentrates and preparing a medicinal solution of the concentrates as well as a method for preparing a medicinal solution from several concentrates.

2. Description of the Prior Art

Patients in renal failure suffer from restricted functioning of the kidneys so that the required excretion of urine-bound substances from the patient's body is prevented. Toxic metabolites must be removed from the patient by purifying the blood in a dialysis treatment. In dialysis, the blood is purified through a mass exchange membrane which comes in contact with the patient's blood on one side and with a cleaning fluid on the other side. The cleaning fluid is the so-called dialysis solutions which take up certain substances intended for secretion and remove them from the patient's blood. In general, dialysis solutions consist of an aqueous composition of physiologically important dissolved components, electrolytes, buffers or osmotically active reagents such as glucose, for example.

In peritoneal dialysis (PD), the dialysis solution is infused into the peritoneum of the patient. The patient's diaphragm then serves as a mass exchange membrane through which the blood is purified. The mass transport is determined by diffusive transport processes of urinary substances from the blood side through the diaphragm membrane and into the peritoneum, which is filled with dialysis solution. An osmotic agent is added to the dialysis solution, so that a higher osmotic pressure prevails in the peritoneum than in the blood. Based on the osmotic pressure gradient, there is a transfer of water through the membrane into the space of the peritoneum. In the course of the treatment or toward the end of the treatment the peritoneum is emptied and the dialysis solution is discarded.

In hemodialysis (HD) the patient's blood to be cleaned is passed through an extracorporeal blood circulation and brought in contact with a mass exchange membrane. The opposite side of the mass exchange membrane is brought in contact with dialysis solution, so that membrane-permeable substances can be removed from the blood by membrane transfer with the dialysis solution. The process of mass transfer can take place through diffusive or convective transport processes in the conventional HD therapies. Through convective transport processes in particular it is possible to withdraw fluid from the patient, so that a solution for HD dialysis must in general have a lower osmotic pressure for cleaning of the blood than solutions suitable for PD dialysis.

In the case of both HD and PD dialysis, the dialysis solutions contain typical dissolved substances, for example:
- electrolytes Na, K, Mg, Ca to maintain an acceptable electrolyte balance for the patient;
- buffers (for example bicarbonate, acetate, lactate . . . );
- glucose (or other osmotic agents) as osmotic agent in peritoneal dialysis or for maintaining the blood sugar level during hemodialysis;
- acids or salts of acids (for example HCl and/or Cl$^-$, acetic acid, citric acid, . . . ), which might contribute toward neutralization of basic partial dialysis solutions or as counterions in the electrochemical equilibrium.

The substances used for the dialysis solution cannot in general be stored in a ready-to-use mixture because the substances may cause mutual degradation. The required stability in storage of a component may presuppose storage conditions which result in degradation of other components. For example, glucose, depending on its concentration in solution, is storable for prolonged periods of time without being subject to unwanted degradation processes to an excessive extent only at a certain acidic pH. At the same time, the compound sodium bicarbonate, which is often used as a buffer in dialysis solutions is not stable in storage under such acidic conditions because bicarbonate tends to decompose as a function of the pH and can release $CO_2$. Under decomposition conditions, the concentration of bicarbonate changes, which is unacceptable from a therapeutic standpoint. The increase in the $CO_2$ partial pressure also makes demands of the medical dialysis equipment leading to technical problems.

A variety of alternative compositions, storage conditions and dosage forms of dialysis solutions or concentrates are known which enable a prolonged storage. It is known that the solution components can be divided into a combination of partial solutions or concentrates so that only acceptable components of a partial solution or of a partial concentrate are stored together. For peritoneal dialysis solutions, a first partial solution comprising glucose, which assumes the function of the osmotic agent, is usually stored at an acidic pH with additional electrolytes, for example, sodium, calcium, magnesium. Another basic or buffered partial solution is necessary to supply a physiological mixed solution that is ready-to-use at least for treatment from the first part and the second part when using the first acidic partial solution. The second part often consists of a solution or a concentrate of sodium bicarbonate and sodium chloride. The partial solutions or concentrates are stored in multiple containers or in multiple chambers of one container. The partial solutions or partial concentrates are present separately so that there is no mutual influence. Immediately prior to use of the dialysis solution, the separate partial solutions or partial concentrates are mixed, possibly adding additional aqueous components, and supplied for the treatment.

In hemodialysis the partial solutions or partial concentrates are often mixed in the dialysis machine before and during the course of the treatment and prepared to yield a finished dialysis solution. Partial concentrates in solid or liquid form which are present in individual containers and are diluted through a connection to the dialysis machine with the help of a prepared hydraulic system are mixed and prepared to the finished ready-to-use dialysis solution. For this purpose partial concentrates in solid or liquid form are often used; these are present in individual containers and are diluted, mixed and processed to yield the finished ready-to-use dialysis solution through a connection to the dialysis machine with the help of a prepared hydraulic system.

Other developments in dialysis have tended toward keeping the necessary concentrates in a single container. First of all, this simplifies preparation and handling of the containers, and secondly this also simplifies the hydraulic system of the dialysis machine because in the meantime only one holding unit is necessary for the partial solutions and fewer connections are necessary to process the solution through the hydraulic system. This trend can be observed in particular in acute dialysis because a greater mobility of the treatment system is required there.

In another variant dialysis solutions for hemodialysis are not prepared from concentrates during the course of the treatment but instead the total required volume of the dialysis solution is prepared in one batch in a step prior to the treatment. The batch is kept on stock in a tank which is prepared to be connected to a dialysis machine. In many cases the tank is an integral component of a dialysis treatment unit or in certain cases can also be moved again separately from it. Batch dialysis may thus have the advantage of selecting the treatment site relatively independently of location through a single preparation of the batch. Treatment stations at various locations can thus be used without having to rely on a preparation unit of dialysis solution or a water connection but supplies the required water for dilution of the concentrates. In these cases, the dialysis solution is mixed together from concentrates at an apparatus provided for this purpose and then is usually stored in a mobile tank.

It is known that the required concentrates for preparing a dialysis solution batch may be kept in just one drum unit. Thus, for example, there are known dry concentrates whose granular particles have a multilayer or multicomponent structure. Each layer of granules or each component contains the substances needed for preparation of the dialysis solution.

In another development different dry concentrates are placed in a drum unit. Various granules corresponding to different solution components are poured into a container layer by layer. The components in one layer are thus present essentially separately from the components of the next layer. Then they are in contact with components of the neighboring layers only through the interfaces between two neighboring layers.

However, in reviewing these developments, it has been found that even in the case of such a layered structure of a granular particle or in a layered presentation of dry concentrates of corresponding solution components, negative interactions may occur among the various concentrates.

Dry concentrates make increased demands in storage in comparison with partial solutions or solution-type partial concentrates. The dry concentrates must not only overcome the aspect of degradation of parts of the concentrates of the solution components during their guaranteed storage time but must also be able to fulfill the aspect of good solubility with a diluent. Observations from the state of the art in storage of dry concentrates have shown that particulate concentrates may undergo agglomeration under the influence of moisture. In an agglomerated state, however, the concentrate is not readily miscible with another aqueous diluent, so that the solution times of such concentrates in clinical use may not be acceptable. The prerequisite is thus that concentrates, in particular when they are dry concentrates, must be rapidly and thoroughly miscible with diluents or other solutions.

An all-purpose concentrate, which contains all the ingredients required for dialysis, is not usually stable in storage. Therefore the concentrate is separated into partial concentrates so that only solution components that are compatible and stable in storage with one another are present in each partial concentrate. A set of concentrates or partial solutions prepared for producing medicinal solutions may thus consist of two, three or more partial concentrates or partial solutions which are stored in a container or bag.

EP 1 458 433 discloses a concentrate container in which the solution components or partial concentrates are arranged in layers and therefore mutually incompatible components are separated from one another.

EP 1 059 083 discloses granules in which the grains have a layered structure. Mutually incompatible solution components can be kept separate from one another by soluble buffer layers.

WO 2007/144427 discloses a system for producing dialysis solutions using a multichamber bag containing a partial concentrate in each chamber. By adding a fluid, the dividing lines between the chambers are broken and the dialysis solution is prepared.

U.S. Pat. No. 4,386,634 discloses a large-volume container, in which dry concentrates for preparing a dialysis solution are stored. By adding water a liquid concentrate is prepared.

U.S. Pat. No. 7,544,301 and EP 0 846 470 disclose methods for monitoring the dissolving process in the preparation of a batch of a dialysis solution based on electrical conductivity measurements.

It is described in the state of the art that different partial concentrates or partial solutions may be used for preparation of dialysis solutions in a multicompartment container. Adequate stability in storage cannot be achieved in storage of the components of the solution, divided among various partial concentrates or partial solutions. The partial concentrates or partial solutions are stored in different containers or in different chambers of a container. The chambers are separated from one another by separating means. The contents are released by dissolving the separating means and yield a finished ready-to-use medicinal solution by aqueous dilution or simple mixing, for example.

For monitoring the preparation process of medicinal solutions, it is important to have clarity about whether all the partial concentrates were mixed in the process. In general the dissolving process and/or dilution process of the partial concentrates is easy to monitor by measuring the electrical conductivity. If the partial concentrates contain ionic substances, then they make a contribution toward the electrical conductivity when dissolved and/or diluted. An end to the dissolving process may be indicated in particular by achieving a final conductivity value in the solution/dilution process. It is thus possible to reliably conclude that all partial concentrate parts or solution parts have been mixed and no other partial concentrates or partial solutions are present in undissolved and/or unmixed form. Similarly, a conductivity value, which does not correspond to a previously defined final conductivity value indicates that a partial concentrate or partial solution may not have been diluted and/or mixed. A monitoring unit may thus be used in an action mode so that an alarm or additional dissolving steps are initiated, for example.

However, the conductivity measurement may provide inadequate information if individual concentrates make only a very minor contribution to the conductivity or none at all. In the worst case, a final conductivity value may already be indicated in the process of preparing the solution, although components of the solution which do not make any contribution toward the electrical conductivity are undissolved, unmixed or undiluted. Solution components which are used for medicinal solutions and can make only a minor contribution toward the electrical conductivity of an aqueous mixed solution or none at all, for example, organic substances, may include:

active ingredients, pharmaceutical drugs;
in particular osmotic agents in the dialysis field: glucose, fructose, galactose, amino acids; acids: acetic acid, citric acid, lactic acid, succinic acid, fumaric acid, oxalic acid, malic acid . . . .

In this technical context the term "low electrical conductivity" is understood to refer to aqueous solutions which have a conductivity value of 0.5 mS/cm or lower. Or these are compositions, for example, concentrates with or without diluents or partial solutions or suspensions, which cause a conductivity change of 0.5 mS/cm or less in an expected solution after dilution. In this sense, the aforementioned organic acids are also to be classified as substances which make this low conductivity contribution to the total solution, depending on the concentration.

Thus there is the problem of monitoring the dissolving process of multiple concentrates, solutions or partial solutions by conductivity measurements, such that at least one of the concentrates consists of substances which do not make any contribution toward the electrical conductivity in the ready-to-use solution.

SUMMARY OF THE INVENTION

The object of the present invention is to refine a medical method and a medical container such that in preparation of a medicinal solution from a diluent and a plurality of partial concentrates, at least one partial concentrate of which makes little or no contribution toward conductivity, it is possible to conclude plausibly by determining a final conductivity value that all partial concentrates or partial solutions have been dissolved or mixed to prepare a ready-to-use solution.

This object is achieved by the subject matter described herein, i.e., a container for storage and preparation of a medicinal solution from a plurality of concentrates or partial solutions, as well as a method for preparing a ready-to-use medicinal solution using the inventive container. Preferred embodiments of the invention are represented by the features thereof described herein.

Thus in an inventive dissolving process a diluent is introduced into a filling chamber in a multichamber container. The container also contains a plurality of concentrate chambers which hold partial concentrates for the preparation of the ready-to-use solution. In the course of filling, the concentrate chambers are broken open and partial concentrates become mixed with the inflowing diluent. In the course of the dissolving process, a change in the electrical conductivity occurs and can be recorded by a suitable measurement device. By arranging the concentrate chambers and inflow ports for the inflowing diluent and the selected geometry of the container, the result may be a predetermined sequence in the release of the partial concentrates. A concentrate chamber holding a partial concentrate which makes little or no contribution toward the electrical conductivity of the ready-to-use solution will be broken open at the same time as or before a concentrate chamber containing a partial concentrate that makes a contribution toward the electrical conductivity of the ready-to-use solution. By monitoring the electrical conductivity in preparation of the solution, through the release of the partial concentrates having little or no contribution toward the electrical conductivity of the ready-to-use solution, it is possible to monitor which concentrate which thus correlates with the release of the partial concentrates that make a contribution to the electrical conductivity of the ready-to-use solution.

BRIEF DESCRIPTION OF THE DRAWINGS

Additional details and advantages of the invention will now be described in greater detail through the exemplary embodiments depicted in the drawings, in which.

DETAILED DESCRIPTION OF THE PREFERRED EMBODIMENTS

Figure 1:
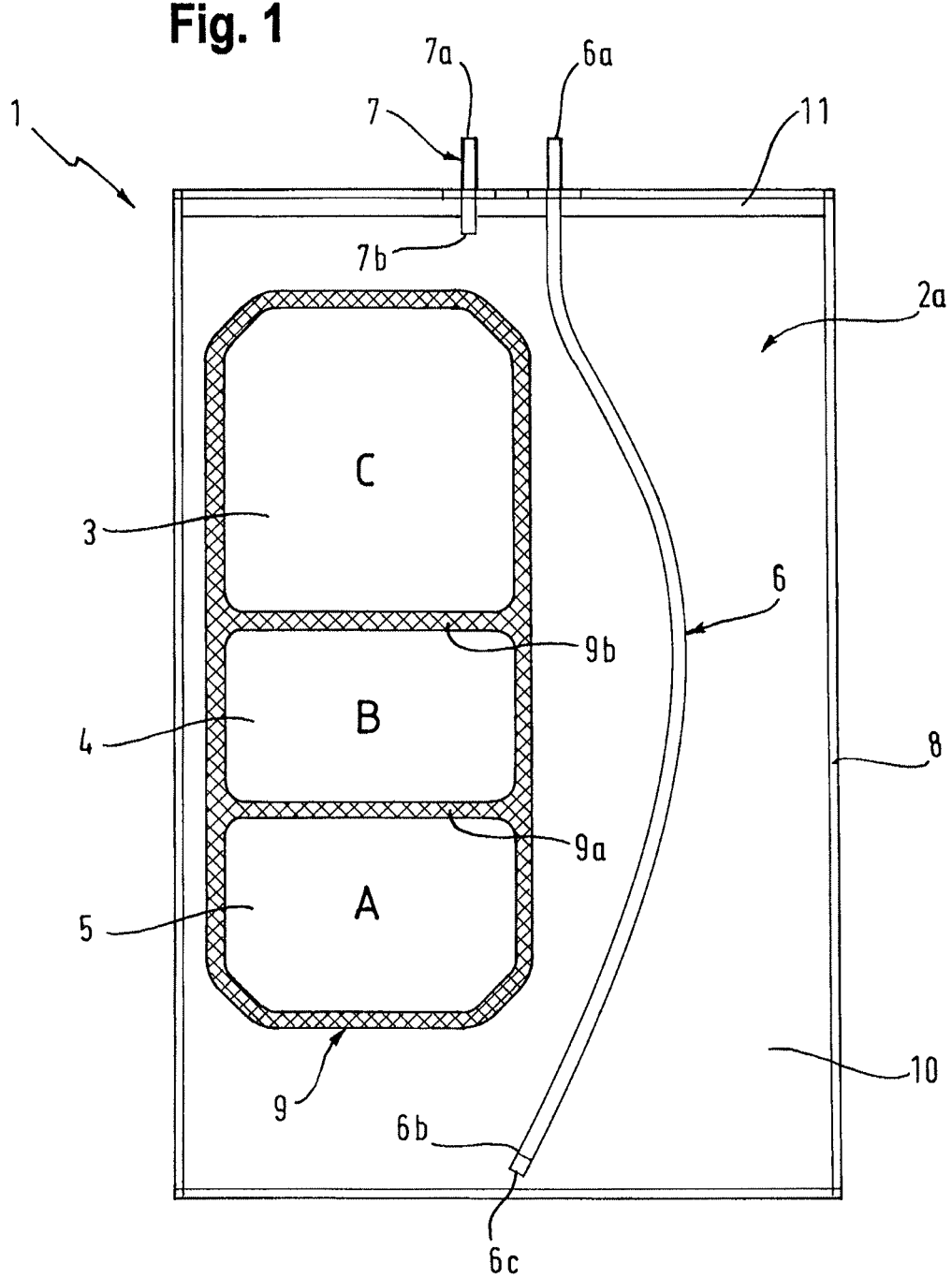
FIG. 1 shows an inventive container having three chambers, which contain solution components.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

In the present invention, a multichamber container (1, 201, 401, 501, 601, 701) and a method for preparing a medicinal solution, in particular a dialysis solution, are described. Starting from partial concentrates (A, $B_1$, $B_2$, C, C1, C2) or partial solutions, a ready-to-use medicinal solution is prepared by mixing partial solutions and/or by adding an aqueous diluent.

The container according to the invention has at least one filling chamber (10, 210, 410, 510, 610, 710) and at least two additional chambers (3, 4, 5, 203a, 203b, 204a, 204b, 205a, 205b, 403, 404, 405, 503, 504, 505, 603, 604, 605, 703a, 703b, 704, 705), which contain concentrates (A, $B_1$, $B_2$, C, $C_1$, $C_2$)/partial concentrates or partial solutions which are incompatible with one another. The chambers are referred to below as concentrate chambers, which is to be understood to mean that they contain concentrates which supply the parts for preparing the ready-to-use medicinal solution by mixing them with a diluent. A "concentrate" is understood in this context to be dry substances in powder form, tablets or granules. Likewise, the term concentrate also includes substances combined with water, which may be in suspension or emulsion, as a concentrated liquid form or in an aqueous solution.

The term "container" as used below is understood to refer to any type of hollow vessel made of flexurally rigid or flexible wall materials also comprising bags in particular.

In general a bag is understood to include containers whose wall material comprises a flexible material, such that the containers collapse under their own weight and are thus considered to be collapsible containers. The collapse of a bag is regarded as an essential structural feature of the bag. In particular bags may be filled with fluids or emptied without any pressure equalization due to the collapsible characteristic of the walls.

Containers with a semirigid wall material, which do not collapse under their weight but are deformable by manual force are also covered by the term "container."

The inventive containers (1, 201, 401, 501, 601, 701) or bags may consist of two opposing outside walls (2a, 2b, 202a, 202b, 402a, 402b, 502a, 502b, 602a, 602b, 702a, 702b) and may be manufactured, for example, from film materials by using welding molds or other methods, for example, extrusion blow-molding methods. Welds may circumscribe the outer contour or circumferential line in at least some sections (8, 208, 408, 508, 608, 708) of the container or bag and may thus define an interior space having a predetermined volume.

The container (1, 201, 401, 501, 601, 701) is a multichamber bag made of flexible film sections (2a, 2b, 202a, 202b, 402a, 402b, 502a, 502b, 602a, 602b, 702a, 702b) in one preferred form. A bag may also be understood to include a container designed so that sections of the container comprise a flexurally rigid material while other sections comprise a flexible film material.

The inventive container or bag has dividing lines (9, 9a, 9b, 209a, 209b, 209d, 209e, 209f, 409, 409a, 509, 509b, 609a, 609b, 609, 709a, 709b, 709c, 709d) which subdivide the container into a plurality of chambers. The dividing lines preferably consist of weld lines or adhesive lines which join opposing sides of a container or bag to one another. Semipermeable sections of the dividing lines are constructed so that they are soluble by applying force or pressure without damaging the circumferential walls of the container. Likewise, when using flexurally rigid containers, the definition of the semipermeable dividing lines also includes material sections which serve as intended breaking points by application of force or pressure and which expose a fluid carrying passage between two compartments. Alternatively, other dividing lines having semipermeable sections may also be used. These also include welding lines with so-called breaking connectors welded in, which are released by manual force. Likewise, welded film sections as partitions may also form this dividing line and are in turn constructed so that they rupture when a force is applied. Alternatively, a dividing line is also understood to be a mechanism which holds together the film sections along a line through a clamping mechanism or folding mechanism and which prevents unintentional mixing of the chamber contents.

The dividing lines (9, 9a, 9b, 209a, 209b, 209d, 209e, 209f, 409, 409a, 509, 509b, 609a, 609b, 609, 709a, 709b, 709c, 709d) subdivide the multichamber container into at least one filling chamber and at least two concentrate chambers. At least one first chamber and one second chamber are divided by at least one first dividing line (9, 9a, 9b, 209a, 209d, 409, 509, 609, 709a, 709c) from the filling chamber (10, 210, 410, 510, 610, 710). The first dividing line may consist of a permanent or semipermanent dividing line in some sections or may be formed completely by a semipermanent dividing line. In particular it may cooperate with a section of a permanent circumferential line of the container (8, 208, 408, 508, 608, 708). The concentrate chamber (3, 4, 5, 203a, 203b, 204a, 204b, 205a, 205b, 403, 404, 405, 503, 504, 505, 603, 604, 605, 703a, 703b, 704, 705) are enclosed by the semipermanent dividing line and sections of the permanent circumferential line (8, 208, 408, 508, 608, 708) and are delineated with respect to the filling chamber. In one embodiment the concentrate chambers are completely surrounded by a bordering line which may consist of the circumferential line (408, 608) permanently in some sections or may consist of the first dividing line (409, 609) semipermanently.

Alternatively, the line of the one first chamber (4, 204a, 204b, 504, 704, 705) surrounding the concentrate chamber and the line surrounding a second chamber (3, 203a, 203b, 503, 703a, 703b) may also be completely surrounded by the one first semipermanent separating line (9, 209a, 209d, 509, 709a, 709c) in at least some sections without cooperating with the circumferential line (8, 208, 508, 708) of the container. The one first dividing line of the chambers then forms a closed line which borders the one first chamber and the one second chamber on the sides. In addition, concentrate chambers are bordered by the outside walls (2a, 2b, 202a, 202b, 402a, 402b, 502a, 502b, 602a, 602b, 702a, 702b) of the container so that the chambers are bordered on all sides.

The one first dividing line (9, 209a, 209d, 409, 509, 609, 709a, 709c) is that the rest may be of such a type that it is designed to be completely semipermanent in a section in which it borders the one first chamber (4, 204a, 204b, 504, 704, 705) and the one second chamber (3, 203a, 203b, 503, 603, 703a, 703b). This yields the advantage that dissolving or breakage of the dividing line in this section by application of force eliminates the border between the two chambers and releases the contents of the chamber. In particular it is such that an initial breakage of the semipermanent dividing line sections requires a higher force than further tearing of the dividing line that has already been broken open at one location. If there is a breakage in the one first dividing line in a section bordering the one first chamber, then there is also a high probability that the bordering section of the one second chamber will also be broken open.

For the process of preparing the medicinal solution in the inventive container, a feed port (6, 206, 406, 506, 606, 706) is provided, this feed port being cut into the circumferential line (8, 208, 408, 508, 608, 708) of the container and optionally bringing the filling chamber of the container into fluid connection with an outer fluid source.

With upright storage of the bag, a diluting liquid, for example, water or partial solution is first introduced into the filling chamber (10, 210, 410, 510, 610, 710) through a feed port. The hydrostatic pressure which acts on the bordering planes (2a, 2b, 202a, 202b, 402a, 402b, 502a, 502b, 602a, 602b, 702a, 702b) in the interior of the container thereby increases due to the filling, and causes at least opening of the first dividing line (9, 209a, 209d, 509, 609, 709a, 709c). The contents of the first concentrate chamber (4, 204a, 204b, 504, 604, 704, 705) are mixed with the inflowing diluent or, alternatively, with an inflowing partial solution. At the latest through further filling of the container, the first dividing line is opened further so that the contents of the one second chamber (3, 203a, 203b, 405, 503, 603, 703a, 703b) come in contact with the inflowing diluent/partial solution and are mixed there. The first semipermanent dividing line is opened in at least some sections, this opening being caused by the buildup in pressure, which in turn causes the opening of the one first chamber and the one second chamber either simultaneously or sequentially.

The filling chamber may surround the enclosed concentrate chambers in the interior of the bag in one embodiment so that when the first and second concentrate chambers are broken open, the concentrates enter directly into the dilution chamber filled with diluent. The filling chamber is preferably in the initial state, an empty chamber which is in direct fluid connection with the feed port.

The semipermanent section of the dividing line is preferably designed so that the dividing line opens merely through the hydrostatic pressure of the filling without requiring any further application of force.

It is thus largely ensured that both chamber contents will come in contact with the inflowing diluent/partial solution and be mixed to form a medicinal solution. Thus it is also possible to be largely certain that the chamber contents of a first chamber containing the concentrates, which do not contribute to the electrical conductivity, are introduced completely into the solution when the dissolving process of the chamber contents of a second chamber containing components which contribute toward conductivity is confirmed by conductivity measurements.

The container may also comprise another third concentrate chamber (5, 205a, 205b, 403, 505, 605). This is advantageous in particular when the solution components must be separated into at least three concentrate parts for stability reasons. A third concentrate chamber may be arranged in the container so that the one first concentrate chamber (4, 204a, 204b, 504, 604), the one second concentrate chamber (3, 203a, 203b, 503, 603) and the one third concentrate chamber (5, 205a, 205b, 505, 605) are surrounded by the one first dividing line (9, 209a, 209d, 509, 609) or the chambers are surrounded in cooperation with the outer circumferential line (8, 208, 508, 608). A hydrostatic pressure, which builds up when filling the filling chamber causes the first dividing line, which is semipermanent in at least some sections to be broken open and the chamber contents (A, B, C, $C_1$, $C_2$) of the one first concentrate chamber, of the one second concentrate chamber and of the one third concentrate chamber to be dissolved. The dissolution of a concentrate of one of the three chambers consisting of solution components which do not make any contribution toward the electrical conductivity is thus monitored by conductivity measurement over the dilution/mixing process of the other chambers which make a contribution toward the electrical conductivity. The dividing line is semipermanent in at least one area which at the same time separates all three chambers from the filling chamber.

The container is preferably a bag which is produced from film material. Sections may be produced from a flexurally rigid material. According to an alternative embodiment, a side wall of the bag is made from a flexurally stiff material. The flexurally stiff side wall imparts a supporting structure to the bag. The flexurally stiff side wall may be an advantage in the case of bags with a large volume in particular and may impart greater stability to the bag. The bag is preferably made of plastic materials, in particular thermoplastic and thermoplastic elastomer plastic materials. Preferred types of polymers include polyolefins and poly-alpha-olefins as well as hydrogenated styrene block copolymers. Polymer grades such as polypropylene, polyethylene, copolymers of ethylene, propylene, butene, hexene or octene, styrene-isoprene-styrene block copolymer (SIS), styrene-ethylene-butylene block copolymer (SEBS), styrene-ethylene-propylene block copolymer (SEPS) and additional types are preferably used in this context.

If the container consists of a bag, there are advantages for the construction of the dividing lines. It is known that multichamber bags are manufactured by permanent bordering welds and peelable seams in the chamber dividing area. Peelable seams in this context are understood to be joints joining to partners, which exert an adhesive effect on one another due to a heat treatment. In the preferred case, the joining partners are two opposite film pieces of a bag which are joined together in the welding process using a welding jaw by the action of heat and contact pressure. The welding temperature determines the force with which the peelable seam can be opened. A peelable seam is understood to be an adhesive bond which can be released again by the action of force without resulting in a complete breakage of the film material. In special embodiments, a peelable connection may also be understood to be a connection which causes a partial delamination of a multilayered film composite due to the action of force. In these cases it is important that the delamination tear does not cause a complete breakage of the film material that would render the bag useless.

In the present case, alternative embodiments are provided for the one first dividing line in the inventive multichamber bag. In a first embodiment the dividing line consists of peelable and therefore semipermanent dividing lines in some sections. Opening of the peelable seams under application of force or through fluid pressure causes the contents of the chamber to be released and subsequently mixed with the diluents or partial solutions flowing in. Permanent sections in the dividing line area connect the walls of the bag even in a filled state. This can impart stability to the bag because a rupture pressure which acts on the circumferential welds when the bag is full is reduced. In the case of large-volume bags, larger than 5 liters in particular, this is important for the stability of the bag.

In another embodiment the dividing lines are made completely of peelable seams. Dissolving the seams in filling the bag allows a good and thorough mixing of all the chamber contents and simplifies the production of the dividing lines from the standpoint of production technology.

The peelable character of the dividing lines is influenced by the welding process. Depending on the temperature of the welding tool, peelable seams which are releasable at a lower force can be produced. At a higher temperature of the welding tool, peelable seams having a higher strength are obtained. Peelable seam strengths are determined by known methods and standards. The peel seam strength is conventionally determined by a T-peel test, in which two film test strips are placed one above the other and welded in one section. The loose strip ends are clamped in gripping jaws of a testing machine so that the test strip bond describes a T. Next, a tensile test is performed on the film composite. The tensile test may be performed in compliance with EN ISO 527-3. Likewise, the standards ATSM F 88-07, ASTM D 1876-01 describe methods for determining the peel seam strength.

For the peel character of a dividing line produced at a defined temperature of the welding tool, the composition of the film layers which are bonded to one another by the heat treatment is also important. In particular a mixture of a thermoplastic polymer and an elastomeric polymer has proven successful. An exemplary embodiment is a composition of 80% of a thermoplastic polypropylene (PP) and 20% of a hydrogenated styrene block copolymer, for example, a thermoplastic elastomer constructed of polymer blocks and styrene and ethylene-butylene (SEBS). The hetero-phase mixture of the polymers supplies peelable weld lines at low temperatures and permanent weld lines which can be released only by breaking the film, at higher temperatures.

Depending on the specific application of an inventive bag, different peel seam strengths may be necessary. In one case, an inventive multichamber bag may be present with liquid concentrate in one of the chambers and the bag may be provided so that the peel seams can be opened by applying an external pressure. In such a case, pressure is exerted on the liquid in a chamber by applying pressure with the hand or by rolling the bag so that the resulting liquid pressure breaks open the adjacent peel seam. Such a bag usually requires a higher peel seam strength because pressure may already be applied to the liquid in a chamber as a result of vibration during shipping so that the adjacent peel seam could be damaged. In this case, the peel seam strengths may be:
  2-20 N/15 mm, preferably 2-15 N/15 mm, preferably 2-10 N/15 mm, 3-18 N/15 mm, 2-5 N/15 mm.

If these multichamber bags with solid concentrates in one or more of the individual chambers are used, there is no risk of unintentional opening of the peel seams because an external pressure due to granular or powdered concentrates inside the chamber, for example, does not propagate and act on the dividing lines. In general, lower peel seam strengths may be selected. In particular there are applications of multichamber bags in which the peel seams are released by an internal pressure of an inflowing liquid. In such cases, a low peel seam strength is again advantageous, so that the concentrate chambers can be broken open with no problem and there is complete mixing of the contents with the inflowing liquid. In such applications, the following peel seam strengths are advantageous:

0.1-6 N/15 mm, preferably 0.2-5 N/15 mm, preferably 0.2-4 N/15 mm, preferably 0.3-2 N/15 mm.

For reasons of stability, different partial concentrates may be stored in three concentrate chambers for preparing medicinal solutions. Likewise, the solution components of medicinal solutions may each be stored individually in a separate concentrate chamber. Thus there may be a plurality of chambers corresponding to the number of solution components required. In addition, it may be advantageous for reasons of solution preparation, for example, more rapid dissolving of several small concentrates, to store the concentrates in more than two chambers.

According to the invention at least two concentrate chambers are bordered by a first dividing line with respect to the filling chamber. Alternatively, at least three chambers may be bordered by a first dividing line with respect to the filling chamber. Alternatively, four chambers may also be bordered by a first dividing line with respect to the filling chamber. Optionally five, six, seven, eight concentrate chambers may be bordered by the one first dividing line with respect to the filling chamber. An embodiment in which the at least two or three or four of the aforementioned concentrate chambers are surrounded by the one first dividing line along the closed line and bordered with respect to the filling chamber is also preferred.

It is advantageous if at least two concentrate chambers (4, 204a, 204b, 404, 504, 604, 704, 705, 3, 203a, 203b, 405, 503, 603, 703a, 703b) which are bordered by the one first dividing line (9, 209a, 209d, 509, 709a, 709c) with respect to the filling chamber are separated from one another by a second dividing line (9b, 209g, 209f, 409a, 509b, 609b, 709b, 709d). The second dividing line may be in the form of a permanent weld or a semipermanent weld or a peelable weld in bag embodiments. In the first case after the first dividing line is released, there remains a weld web forming the second dividing line that separates the chambers and may contribute toward stabilization of the filled bag. In the second case the peelable second dividing line is also divided by the application of pressure, for example, external application of pressure or internal filling pressure so that the opposing film sheets of the bag are no longer connected to one another.

Alternatively, a first, a second and a third concentrate chamber (4, 204a, 204b, 504, 604, 3, 203a, 203b, 503, 603, 5, 205a, 205b, 505, 605) may also be bordered by a first dividing line with respect to the filling chamber and a second dividing line (9b, 209g, 209f, 409a, 509b, 609b) may be present between the first chamber and the second chamber and a third dividing line (9a, 209b, 209e, 509a, 609a) may be present between the second and the third chamber. The second and third dividing lines may each be permanent or semipermanent and may be present as permanent or peelable welds in embodiments of the bag. In the preferred case, the one first, second and third concentrate chambers are enclosed by the one first dividing line. And in the particular preferred case, all the dividing lines are semipermanent dividing lines, in particular peel seams.

Alternatively, in particular in embodiments of inventive bags having four or more concentrate chambers, additional dividing lines may be constructed like the first dividing line to border additional concentrate chambers with respect to the filling chamber. The concentrate chambers may contain concentrates, partial concentrates, liquid concentrates and/or partial solutions. Two or more concentrate chambers of at least four chambers may contain the same or different concentrates, partial concentrates, liquid concentrates and/or partial solutions.

In a preferred embodiment the dividing lines, i.e., the first dividing line, the second dividing line, the third dividing line, etc. may be designed as peel seams and integrally embodied in bag embodiments. In other words, the individual semipermanent dividing lines are not set off from one another but instead develop one into the other or overlap. Peel seams are characterized in that the force applied for a first initial tear in the peel seam is higher than the force applied for additional separation of a peel seam that has already been torn. The integral construction of the sections of the first dividing line, the second dividing line, the third dividing line or additional dividing lines as a cohesive peel seam construction ensures opening of all of these peelable sections because the tear propagation strength of a partially peeled peel seam is reduced. If a section of the peel seam construction has been partially peeled, it is possible to ensure that the additional sections can be opened by applying a lower force.

In addition, the inventive container has a feed port (6, 206, 406, 5006, 606, 706) and/or a discharge port. The feed port allows a fluid, for example, an aqueous diluent to be added to mix the concentrates, the partial concentrates, the liquid concentrates and/or the partial solutions to prepare a medically usable solution, for example, via an external pump. If the container is a bag, then the bag unfolds due to the addition of the diluent. The internal hydrostatic pressure that builds up exerts a tensile stress on the peel seams via the film wall. By additional filling, the first dividing line, the second dividing line, the third dividing line, etc. are released successively according to the degree of filling and the hydrostatic pressure in the interior of the bag and the chamber contents. In the remaining course the chamber contents become mixed with the diluent flowing in through the port so that a usable medicinal solution—preferably a dialysis solution—is obtained after the dissolving process. In another embodiment the container has a discharge port with the help of which the solution thus prepared can be removed for additional applications. There is preferably only one port that may be used for both filling and discharge. According to another embodiment, the discharge/filling port is designed as a length of tubing which passes through the outside walls of the container, for example, through a puncture weld and leads into the inside of the bag. It is preferably for machine-filling operations for the container to be stored upright, for example, stored hanging on an integral holding rail (11, 211, 411, 511, 611, 711) and for the tube of the feed port to lead into the lower part inside the container, so that the container is filled from the bottom. Alternatively, the feed port may also be connected to the container at the bottom when the container is stored upright and then the length of tubing may protrude from the bottom into the inside of the bag to accomplish the filling from underneath. Filling from the bottom is advantageous in upright storage of the container because turbulence can be produced by additional means (6c, 206c, 406c, 506c, 606c, 706c) as the liquid flows into the container, and this turbulence promotes mixing of the concentrates, partial concentrates, liquid concentrates and/or partial solutions.

The container advantageously has a filling chamber into which the feed port protrudes. The filling chamber is first filled and with a rise in filling pressure the dividing lines are released so that the contents of the concentrate chambers are mixed with a quantity of liquid already present. This has the advantage that the contents of the concentrate chamber can be distributed immediately in the quantity of liquid present in the filling chamber and the solution/mixing process is facilitated.

The feed port preferably has means for creating a flow turbulence at the end of the length of tubing inside the container which promotes thorough mixing of the concentrates with the diluent.

In addition, it is advantageous that the container in the embodiment as a bag is made of an elastic extensible film material. The bag thus increases its volume with an increase in filling by the diluent like a balloon. The film walls are stretched elastically so that when the bag is emptied after use of the medicinal solution the stretching is reversed and the empty bag shrinks back to the smallest possible dimension. This yields handling advantages for the nursing staff when using large-volume bags with filling volumes of more than 60 liters. In addition, the use of the stretchable film results in a better filling of large-volume bags because the bag expands without wrinkles as it fills and shrinks largely without wrinkles when it is empty. Thus complete filling and emptying are possible. In addition, the stretchable film lowers the force expended for starting the separation of peelable dividing lines. If too much force is applied in releasing the peel seam, it is absorbed by stretching of the material of the film and thus counteracts possible film breakage and preserves material. One film that is preferred for use for producing an inventive multichamber bag is described in German Patent Application DE 10 2010 014 785.0 the contents of which are referenced fully here. An elastically stretchable multilayer film is described there; it has at least one relatively thin outer layer in relation to the total thickness of the film, which is used for welding and also has at least one relatively thick middle layer based on the total thickness of the film, this middle layer being essentially responsible for the mechanical behavior of the film, in particular its elastic extensibility. The outer layer has two thermoplastic elastomers, one having a high melt flow behavior and the other having a low melt flow behavior. This optimizes the peelability of the peel seams under elastic elongation of the film without making the peel seams too weak for the intended stress and without overstressing the film via the stretching.

The inventive bag is intended for, among other things, being used in a system for producing medicinal solutions. In particular this system involves a device for producing and supplying a ready-to-use dialysis solution. The system comprises:
  the inventive multichamber container with concentrates/partial solution for preparing a medicinal solution, in particular dialysis solutions;
  a control unit for monitoring the preparation of the liquid, preferably by measuring the electrical conductivity;
  additional regulated and controlled pump means which cooperate with the system and allow a diluting liquid to be added to the solution container of the recipient system;
  additionally a supporting structure which is prepared for receiving an inventive multichamber container or multichamber bag for preparing the medicinal solution.

For monitoring the progress of the dissolving process, the system has means for determining the electrical conductivity of a sample taken. However, means for continuously monitoring the conductivity of the mixed solution during the preparation process may also be provided. In one embodiment, the mixed solution obtained in the course of preparation of the medicinal solution and analyzed by means of conductivity sensors may flow through a container or a volume section. The rise in conductivity value during the preparation of the solution is detected by the conductivity sensors and transmitted to a control unit of a processor unit. A conductivity profile for preparation of the solution from multiple partial concentrates/partial solutions may be stored in a storage unit. The type of solution container in the configuration of the partial concentrates may be entered via an input unit and compared with the stored profiles. If the values correspond to the values of the corresponding values stored in the storage unit over time match the other values in the course of preparation of the medicinal solution in the solution container, then the solution is released for further use by the control unit of the processor unit. Otherwise a signal may be triggered by the control unit, indicating that the solution thereby prepared is not released.

In addition, a method for preparing a medicinal solution from multiple concentrates using a multichamber container described previously is also consistent with the subject matter of the invention. According to this method a liquid, for example, RO water, or a partial solution is introduced into the one filling chamber (10, 210, 410, 510, 610, 710) of the container (2, 201, 401, 501, 601, 701). During the filling operation a first semipermanent dividing line (9, 209a, 209d, 409, 509, 609, 709a, 709c) is broken open due to the hydrostatic pressure building up from the fluid introduced and the concentrate of one concentrate chamber (3, 203a, 203b, 405, 503, 703a, 703b) is released and mixed with the liquid in the filling chamber. The released concentrate or the concentrate of a concentrate chamber (4, 204a, 204b, 404, 504, 704, 705) broken open in the remaining course of the filling operation yields essentially no contribution to the electrical conductivity of the solution to be prepared. Such components may be, for example, organic substances which are soluble in aqueous systems such as saccharides, oligosaccharides or polysaccharides, polymeric water-soluble substances or, for example, glucose, fructose, maltodextrin, icodextrin, inulins, etc.

Through additional filling, the one first dividing line or another semipermanent dividing line is then further broken open and the concentrate (C, $C_1$, $C_2$) of an additional concentrate chamber (3, 203a, 203b, 503, 703a, 703b) is released, making a contribution toward the electrical conductivity of the solution. Such substances may be in particular salts which are present in dissociated form in mixture with the diluent, for example, sodium chlorides, magnesium chlorides, calcium chlorides, potassium chlorides, sodium phosphates, sodium citrates, sodium lactates, sodium carbonates, salts of weak acids, for example, lactates, acetates, salts of malic acid, fumarates, oxalates, succinates, carbonates or bicarbonates . . . , or salts of amino acids.

The release of a concentrate making a contribution to the electrical conductivity and a concentrate without any electrical conductivity may take place simultaneously or with an offset in time, but in any case in such a way that the concentrate (A, B) without any contribution or without any characteristic contribution to the electrical conductivity in solution is not released and dissolved after the concentrate with a contribution to the electrical conductivity in solution (C, $C_1$, $C_2$). This method ensures that the dissolving of the concentrate having a contribution to the electrical conductivity is monitored on the basis of the conductivity measurement, so that the dissolving of the concentrate that makes no contribution to the electrical conductivity must already be concluded or takes place concurrently. With the help of this method and using the container described above, complete dissolving of concentrates may be tracked by conductivity measurements, whereby certain concentrates make no contribution to the electrical conductivity. A finished medicinal solution, for example, a dialysis solution preferably has a specific electrical conductivity of 13.6 mS/cm. Depending on the composition of the ready-to-use solution, specific conductivity values of 10 to 15 mS/cm may be expected in the sense of the inventive subject matter.

Concentrates (A, B) which alter the specific electrical conductivity value in solution only to a slight extent, for example, by 0.5 mS/cm or less are considered to be inadequate for allowing monitoring of their dissolving process based on conductivity measurements. Especially in preparation of large-volume supplies of medicinal solutions, for example, a dialysis liquid supply of 60 to 120 liters, the possibility of errors in the preparation process cannot be ruled out. More accurate measurements of electrical conductivity values are possible technically but are not readily feasible within the scope of preparation of a ready-to-use solution from starting concentrates because too many parameters influence the dissolving process and thus the change in conductivity. Changes in conductivity of 0.5 mS/cm or less, for example, 0.3 mS/cm or less or 0.1 mS/cm or less cannot be considered to be characteristic for monitoring of the dissolving process in the sense of the inventive subject matter. Concentrates which still make such minor contributions to the conductivity of the ready-to-use solution are referred to in the sense of the inventive subject matter as concentrates which do not make any significant contribution to the electrical conductivity of a solution to be prepared.

Alternatively, the pressure may also be applied to the bag externally and the required force applied to break the semipermanent dividing lines. For monitoring the preparation of the medicinal solution, here again preferably electrical conductivity monitoring is used.

In a preferred embodiment, a bag is used as the container for implementation of the inventive method. In particular the bag may be a large-volume bag, which is to be understood to be a volume of 5-120 liters.

Use of a bag for the inventive method has the advantage that the bordering dividing lines may be designed as releasable peel seams. Peel seams are easy to manufacture by plastic welding molds from the standpoint of production technology by specifying sealing temperatures which correspond to the film material so that there is no permanent welding of the film pieces. The required peel seam strengths are identical to the peel seam strengths described for the multichamber bag.

Through different designs of the peel seam strengths, sequential rupturing of the concentrate chambers during the filling operation can be influenced. Thus, for example, a peel seam section which borders a concentrate chamber containing concentrates that make no contribution to the electrical conductivity with respect to the filling chamber may have weaker peel seam strengths. A peel seam section which separates a concentrate chamber containing concentrates that make a contribution to the electrical conductivity from the filling chamber may have a greater peel seam strength. The concentrate without a contribution to the electrical conductivity is then released with a lower force than the concentrate which makes a contribution to the electrical conductivity. This meets the requirement, which is relevant in the filling method, namely that concentrates without a contribution to the electrical conductivity must be dissolved before or concurrently with concentrates which do make a contribution toward the electrical conductivity.

Preferred methods are those in which the pressure inside the bag acts by supplying the diluent into the interior of the bag. In this case the diluent, for example, water is supplied by a source, for example, an RO (reverse osmosis) installation. The bag may be produced in an embodiment using dry concentrates with relatively weak peel seam strengths of the dividing lines. This is advantageous because the pressures to be applied to release the dividing lines may be kept low in this way. Accordingly, material strengths of the film used for the bag and the film thicknesses may be selected to be lower, so that it saves on materials and manufacturing costs.

In one embodiment an external pumping means supplies liquid which is directed through a port into the interior of the bag. The internal filling pressure which builds up is built up via the external pump through the access port in the inventive method. With an increase in the liquid pressure in the interior of the bag, the dividing lines are opened, the contents of the chamber are released and become mixed with the inflowing diluent.

The arrangement of the port on the bag and the inflow of the diluent take place in such a way that a first chamber is opened. The chamber contents of the one first chamber preferably include components which do not make any contribution to the electrical conductivity of the mixed solution. These may include organic compounds, for example, glucose, sorbitol, fructose, osmotically active substances such as water-soluble polymers, for example, polyglucoses, polyfructoses and polyethers in particular.

In the remaining course of filling of the bag, another chamber is broken open and the contents of the chamber become mixed with the diluent. The chamber contents are components which make a contribution to the electrical conductivity of the solution. In the case of dialysis solutions, these may be in particular water-soluble salts, for example, sodium chloride, magnesium chloride, calcium chloride, sodium phosphates, potassium chloride, salts of weak acids, for example, sodium lactate, sodium acetate, sodium bicarbonate and/or sodium carbonate or sodium citrate. The conductivity sensor detects an increase in conductivity in the course of the dissolution of the components of this chamber. Depending on the bag design, the one first chamber containing components which do not make any contribution toward the electrical conductivity is opened in the course of, i.e., before or simultaneously with the one second chamber containing components which make a contribution toward the electrical conductivity of the solution, so the opening of the one first chamber is also ensured with the change in conductivity by releasing the one second chamber.

DETAILED DESCRIPTION OF THE INVENTION ON THE BASIS OF THE DRAWINGS

The following examples are embodiments that are consistent with the subject matter of the invention without in any way restricting the subject matter of the invention through these examples. From the context of the description it will be apparent to those skilled in the art that the invention can also be applied even beyond these exemplary embodiments.

In one embodiment of the inventive container for use in dialysis, preferably multiple concentrate parts which are stored in multiple chambers of the bag are used. The concentrates are preferably solid concentrates, but liquid concentrates or other concentrate forms may be used just as well with the inventive bag.

A preferred concentrate composition in an inventive multichamber bag for production of a ready-to-use dialysis solution is obtained from the following table.

The preparation of multiple concentrates for production of a dialysis solution is the subject matter of DE 102010039489.0 to which reference is herewith made to the full contents.

TABLE 1

| Component | Concentrate chamber | Initial weight (g) | Concentration in ready-to-use solution (mml/L) | Contribution to electrical conductivity and solution |
|---|---|---|---|---|
| Basic magnesium carbonate $4MgCO_3 \times Mg(OH)_2 \times 5H_2O$ | A | 3.01 | 0.5 | essentially none present |
| D-glucose anhydrous | B | 62 | 5.55 | essentially none present |
| Calcium chloride anhydrous | A | 8.62 | 1.25 | essentially none present |
| Citric acid | A | 11.97 | 1.0 | essentially none present |
| Table salt | C | 391.22 | 140 | present |
| Sodium bicarbonate | C | 166.78 | 32 | present |
| Potassium chloride | A | 28.1 | 2 | essentially none present |

One or more solution components are divided among three concentrate chambers (A, B, C). Thus:
- glucose is stored in compartment B without any other substances
- the salts magnesium carbonate, calcium chloride, sodium chloride, potassium chloride and citric acid are stored in another compartment A
- sodium chloride and sodium bicarbonate (optionally potassium bicarbonate) are stored in another compartment C.

The components which are preferably combined in concentrate A may physically induce a change in the electrical conductivity in the solution because these are dissociated salts in solution and are therefore charge carriers. However, although these substances are essential in a dialysis solution, they are present in a quantity that is too small to allow a reliable result to be deduced from the measured values based on the solution state of the corresponding concentrate for monitoring of the preparation of the dialysis solution based on a conductivity measurement from the corresponding concentrates. Thus this concentrate A for preparing a dialysis solution must also be regarded as a concentrate which essentially makes no contribution to the electrical conductivity of the finished dialysis solution.

The division of the components into three concentrate parts is done for reasons of stability and storage. In general, it should be noted that no degradation of concentrates takes place during storage. It has been found that solid concentrates of sodium bicarbonate, citric acid and glucose undergo unacceptable changes when stored jointly. Reactions of glucose degradation take place. The dry concentrates tend to pick up water in mixture due to atmospheric humidity, resulting in agglomerates which cannot be dissolved rapidly enough. Bicarbonate salts are therefore to be stored separately from glucose and separately from citric acid. Glucose is also to be stored separately from citric acid. Sodium chloride is likewise to be separated from glucose for storage. The division of the concentrates results in storage of the concentrates in at least three parts, but glucose must be stored in isolation and is therefore a partial concentrate which makes no contribution to the electrical conductivity in solution. Other preferred embodiments will be explained on the basis of the figures.

FIG. 1 shows a container 1 having a circumferential permanent bordering line 8. The container is preferably a bag and the circumferential bordering line is formed from a permanent weld. The bag is composed of an upper outside wall 2a, seen from the perspective of FIG. 1, which is preferably produced from a film sheet. In addition, the container or bag is formed by another lower outside wall 2b which is not shown but is seen from the perspective of FIG. 1. The bag also has a concentrate chamber A with a concentrate 5, another concentrate chamber with concentrate 4, another concentrate chamber C with concentrate 3. The concentrate chamber is surrounded by a first dividing line 9 which is at least partially semipermanent. The first concentrate chamber A is separated from the other concentrate chamber B by a second dividing line 9a which is semipermanent in at least some sections. Concentrate chamber B is separated from the other concentrate chamber C by a third dividing line 9b which is semipermanent in at least some sections. Preferably all dividing lines 9, 9a, 9b are designed to be semipermanent in at least some sections and in an especially preferred embodiment, all the dividing lines 9, 9a, 9b are completely semipermanent. In addition, it is advantageous if the dividing lines are produced by peel seams.

The bag also has a port 7 with a first end 7a outside of the bag and a second end inside the bag. Another port 6 connects the inside of the bag to another end 6a outside the bag via a first end inside the bag 6b. The port 6 is provided for communicating with additional fluid conveyance means, for example, a pump. The ports 7 and 6 are preferably attached by welded connections in the circumferential bordering line 8 in a fluid-tight seal. Means 6c for generating fluid turbulence in the inflowing diluent are preferably provided on the end 6b of the port 6. These means may be designed as a turbulence-generating nozzle or as a turbulence-generating frit.

In addition, port 6 consists of a length tubing which passes through the bag in its longitudinal extent in the interior. It is thus ensured during the filling operation that when the bag is stored upright, for example, by holding the bag on an integral holding rail 11, the bag is filled from the bottom and the concentrate chambers A, B, C are opened by the interior fluid pressure in the order A, B, C.

In one embodiment the concentrate chamber A holds a concentrate 5 consisting of calcium chloride, sodium chloride, potassium chloride and citric acid and making a minor contribution to the electrical conductivity in solution. Concentrate chamber B holds a glucose concentrate 4 which does not make any contribution to the electrical conductivity in solution. Concentrate chamber C contains a concentrate 3 consisting of sodium chloride and sodium bicarbonate, optionally potassium bicarbonate which makes a contribution toward the electrical conductivity in solution.

The bag also has an interior space 10 which represents a filling chamber and is preferably empty. In the preferred bag version of the container, the opposing film sheets 2a, 2b are pressed apart from one another by the inflow of diluent into the filling chamber 10 so that with further filling, a tensile stress is exerted on the dividing lines 9, 9a, 9b and they are released so that the partial concentrates 5, 4, 3 are mixed with the diluent.

Figure 2:
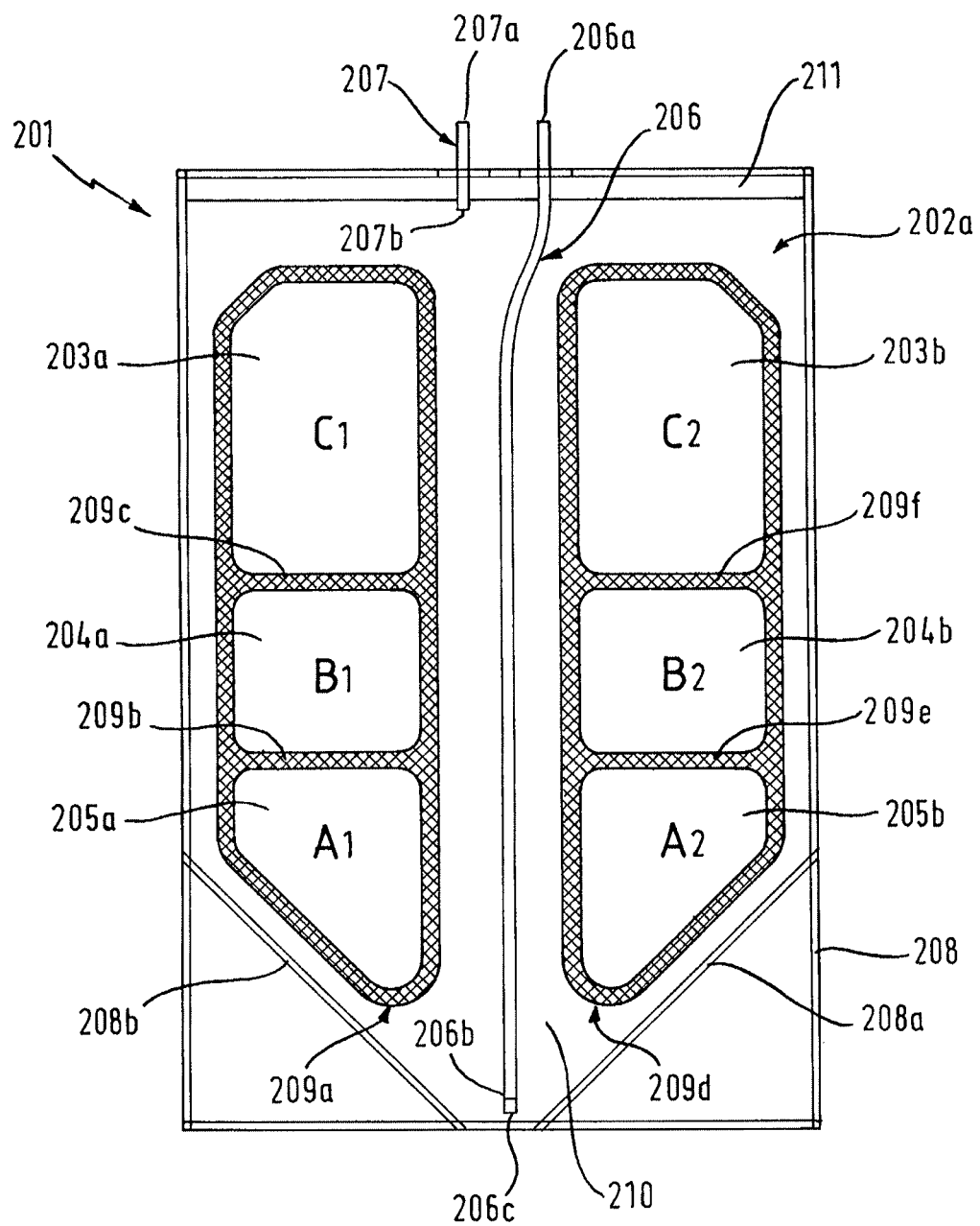
FIG. 2 shows an inventive bag container having six chambers, which contain solution components.

FIG. 2 shows another diagram of a container 201, preferably a bag. The bag is composed of an upper film sheet 202a, as seen from the perspective of FIG. 2, and a lower film sheet 202b (not shown). The bag also has a concentrate chamber A1 with concentrate 205a. According to the information in Table 1, the concentrate chamber A1 contains the substances magnesium carbonate or generally soluble magnesium salts, calcium chloride or generally soluble potassium salts, citric acid or citrate salts. The concentrate 205a makes only a minor contribution to the electrical conductivity in solution.

Another concentrate chamber B1 contains a concentrate 204a. In one exemplary embodiment the concentrate 204a consists of a glucose concentrate which does not make any contribution toward the electrical conductivity in solution.

Another concentrate chamber C1 with a concentrate 203a contains additional substances which are incompatible with concentrates 205a, 204a, i.e., they tend to degradation or enter into unwanted interactions. The concentrate 203a makes a contribution toward the electrical conductivity in solution. In particular the concentrate 203a is sodium chloride or sodium salts and sodium bicarbonate in general or salts of carbonic acid in general.

The chambers are surrounded by a closed circumferential line which is formed by a dividing line 209a which has at least partially semipermanent sections. The dividing line 209a preferably consists of a peel seam. The contents of the concentrate chambers A1, B1, C1 are separated from one another by the additional dividing lines 209b, 209c. The additional dividing lines 209b, 209c may be permanent weld lines, partially semipermanent weld lines or peel seams. In a preferred embodiment the peel seams 209a, 209b, 209c form an integral construction of peel seam sections which develop into one another and are completely releasable.

The exemplary embodiment in FIG. 2 is additionally characterized in that a port 206 connects the inside of the bag 210 via a first end in the inside of the bag 206b and another end outside of the bag 201. Port 206 is preferably attached by welded joints in a fluid-tight manner in the circumferential line 208. Means 206c for generating fluid turbulence in inflowing diluent are preferably provided on the end 206b of the port 206. These means may be embodied as a turbulence-generating nozzle or as a turbulence-generating frit. In addition, port 206 consists of a length of tubing which passes through the bag in its longitudinal extent in the interior of bag 210. It is thus ensured in the bag method that with upright storage by accommodating the bag on an integral holding rail 211, for example, the bag is filled from the bottom and the concentrate chambers A1, B1, C1 are opened in the sequence A, B, C by the internal filling pressure.

Another port 207 with a first end 207a outside of the bag and another end 207b inside the bag serves to remove or supply solutions, substances, medications, etc.

In addition, the embodiment in FIG. 2 has a second set of compartments A2, B2, C2 which are enclosed by another dividing line along a second closed circumferential line 209d. Additional dividing lines 209e and 209f divide the contents of chambers A2, B2, C2. In a preferred embodiment the peel seams 209d, 209e, 209f form an integral construction of peel seam sections which develop one into the other and are completely releasable.

In the exemplary embodiment, the contents of the concentrate chamber A2 consist of a concentrate 205b which makes a minor contribution toward the electrical conductivity in solution. The concentrate 205b in concentrate chamber A2 may be identical to the concentrate 205a or may contain only a portion of the components of concentrate 205a. In one exemplary embodiment, the solution components 205b consist of magnesium carbonate or of soluble magnesium salts, calcium chloride or soluble calcium salts, citric acid or citrate salts or another acid in general.

Another concentrate chamber B2 with solution components 204b contains in one exemplary embodiment the substances which do not make any contribution to the electrical conductivity in solution. In one exemplary embodiment this may include anhydrous glucose. The concentrate 204b may be identical to 204a or may contain other substances which do not make any contribution toward the electrical conductivity.

Another concentrate chamber C2 with concentrate 203b contains additional substances which are incompatible with the substances of the solution components 205b, 204b, i.e., tend to degradation or enter into unwanted interactions. In addition, this concentrate in solution makes a contribution toward the electrical conductivity. If concentrate chamber C2 is broken open and an increase in the electrical conductivity is detected by dissolving of the concentrate 203b, then the concentrate 204b is definitely also dissolved. The substances of the solution components 204b may be identical to the substances 204a or may contain only a portion or additional substances 204a. In particular the concentrate consists of sodium chloride or in general of sodium salts, sodium bicarbonate or in general the salts of carbonic acid.

The embodiment also shows a circumferential line 208 which consists of a permanent weld. Additional permanent weld lines in sections 208a and 208b border the container contents or bag contents so that the result is an inclined bag bottom. This construction facilitates turbulence in the inflowing diluent due to means 206c which produce fluid turbulence and thus it facilitates the dissolving process of components 205a, 205b, 204a, 204b, 203a, 203b.

Figure 3:
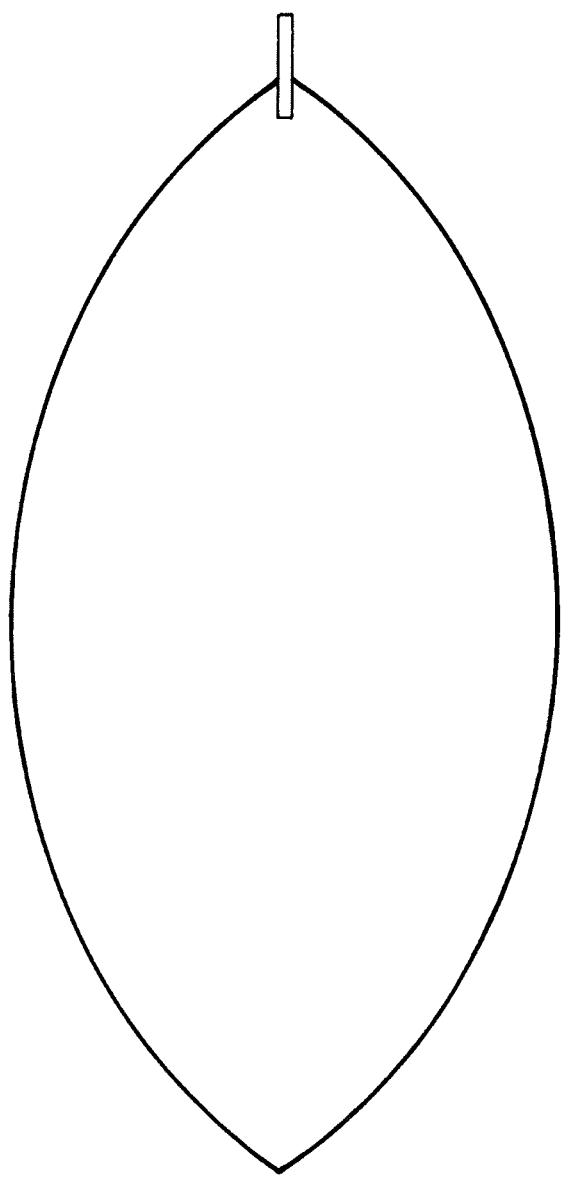
FIG. 3 shows an inventive bag in the filled state after all the chamber dividing lines have been separated.

FIG. 3 shows a lateral cross section of one embodiment in the filled state. In particular this view represents one embodiment in which all the dividing lines are semipermanent and have already been released by the filling.

Figure 4:
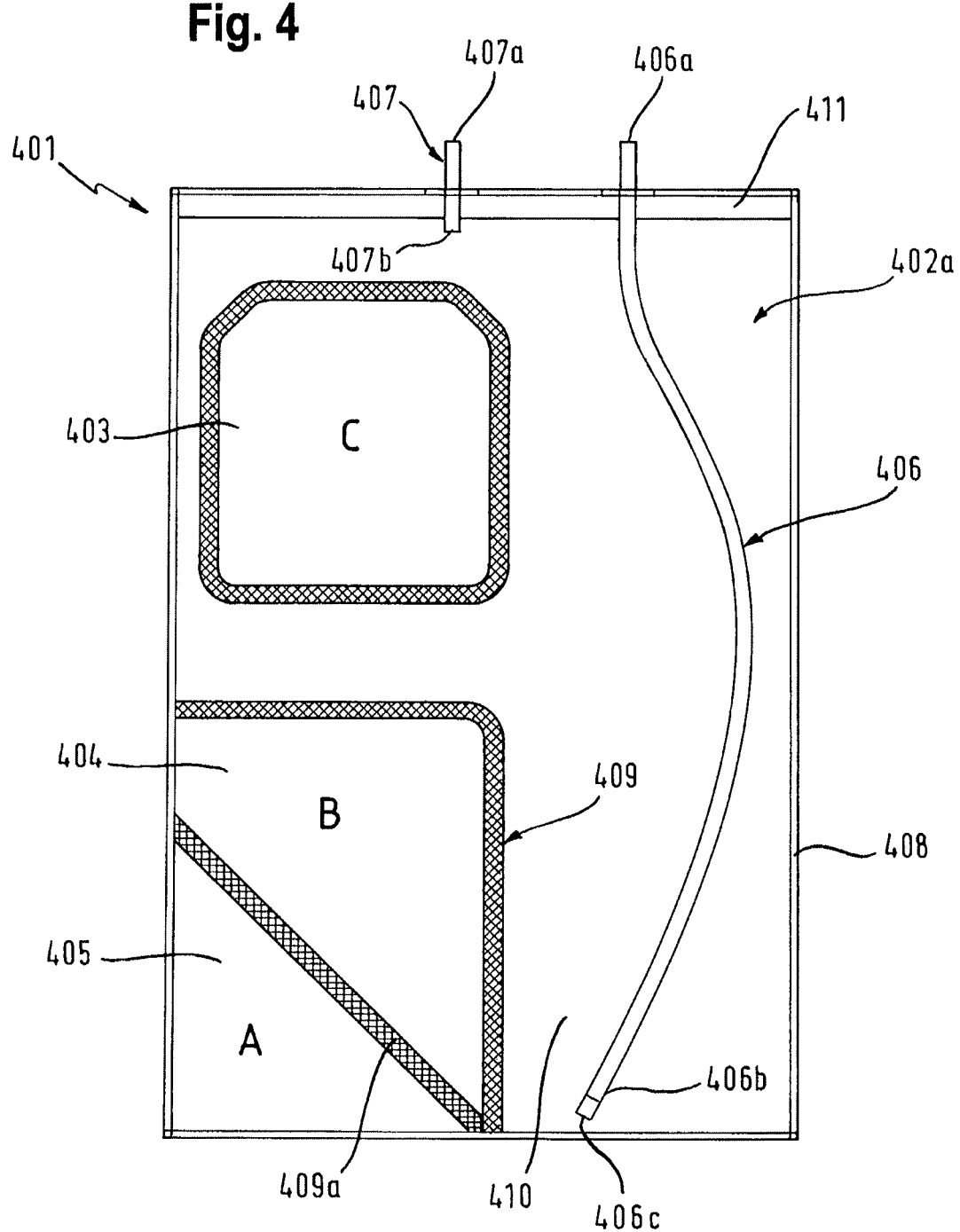
FIG. 4 shows another embodiment of an inventive container having three chambers containing solution components.

FIG. 4 shows another alternative embodiment 401. The container, preferably bag, has an upper outside wall 402a as seen from a perspective in FIG. 4 and a lower outside wall 402b (not shown) which in a preferred version comprises the upper and lower film sheets of a bag. The bag also consists of the concentrate chambers A, B, C with the concentrates 405, 404, 403. The concentrate 405 in chamber A may according to Table 1 be identical to the concentrates 205a, 205b, 5 of the preceding embodiments 1, 201 and may make a minor contribution toward the electrical conductivity in solution.

The concentrate 404 in concentrate chamber B may according to Table 1 be identical to the concentrate 204a, 204b, 4 of the preceding embodiments 1, 201 and does not make any contribution toward the electrical conductivity of the solution.

The concentrate 403 in concentrate chamber C may according to Table 1 be identical to the concentrates 3, 203a, 203b of the preceding embodiments 1, 201 and may make a contribution toward the electrical conductivity of the solution.

Concentrate chambers A and B are enclosed by a circumferential line 409 which is formed in sections from a part of the circumferential line 408 and for the other part from a dividing line which is at least partially semipermanent. Preferably the first dividing line of the circumferential line 409 consists of a peel seam and forms in one section 412a border of the concentrate chambers A and B. The contents of the concentrate chambers A, B are separated from one another by the second dividing line 409a.

The second dividing line 409a is semipermanent in at least some sections and preferably is a completely semipermanent weld line, for example, a peel seam. In the preferred embodiment shown here, the peel seams of the dividing lines of 409 and 409a form an integral construction of peel seam sections which develop into one another so that an incipient peel seam break in the dividing line from 409 is also propagated to the dividing line 409a.

A port 406 connects the inside 410 of the bag via a first end inside the bag 406 and another end 406a outside of the bag 401. Port 406 is attached in a fluid-tight manner in the circumferential dividing line 408, preferably by weld connections. Means 406 for creating fluid turbulence in the inflowing diluent are preferably provided on the end 406b of the port 406.

These means may be designed as turbulence-generating nozzle or as a turbulence-generating foot. In addition, port 406 consists of a tube which passes through the bag in the interior in its longitudinal extent. This ensures that in the filling operation the bag will be filled from beneath, for example, in upright storage by holding the bag on an integral holding rail 411, and the concentrate chambers A, B, C will be opened in the order A, B, C by the internal filling pressure.

Another port 407 with a first end 407a outside of the bag and another end 407b inside of the bag serves to remove or supply solution, substances, medications, etc.

Figure 5:
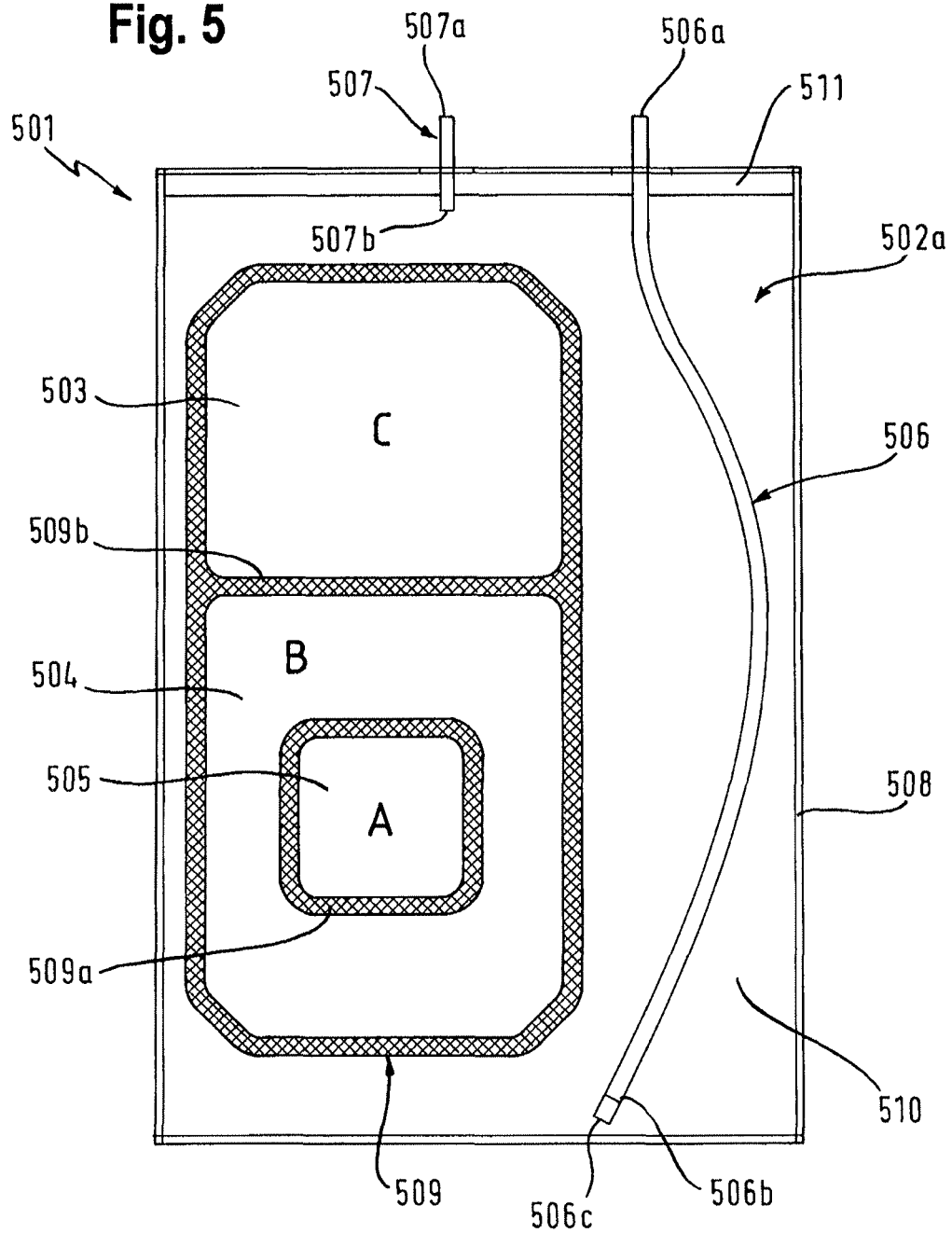
FIG. 5 shows another embodiment of an inventive container containing solution components.

FIG. 5 shows another alternative embodiment. This container, preferably bag, has an upper outside wall 502a in perspective in FIG. 5 and a lower outside wall 502b (not shown) which in a preferred version form the upper and lower film sheets of a bag. The bag also consists of the concentrate chambers A, B, C with the concentrates 505, 504, 503. The concentrate 505 in the concentrate chamber A according to Table 1 may be identical to the concentrates 5, 205a, 205b of the preceding embodiments 1, 201 and may make a lower contribution to the electrical conductivity of the solution.

The concentrate 504 in concentrate chamber B may be identical to the concentrates 4, 204a, 204b of the preceding embodiments 1, 201 according to Table 1 and may not make any contribution toward the electrical conductivity of the solution.

The concentrate 503 in concentrate chamber C may be identical with the concentrates 3, 203a, 203b of preceding embodiments 1, 201 according to Table 1 and may make a contribution toward the electrical conductivity of the solution.

The concentrate chambers A and B are separated by a semipermanent dividing line in at least some sections along a closed circumferential line 509. The dividing line is preferably performed by a continuous peel seam. The contents of the concentrate chambers A, B, C are separated from one another by the additional dividing lines 509a, 509b. A first dividing line 509 borders the concentrate chambers B and C and surrounds chamber A. A second dividing line 509a separates the concentrate chambers A and B. An additional dividing line 509b separates the concentrate chambers B and C. The dividing line 409a is semipermanent in at least some sections and preferably is a completely semipermanent weld line, for example, a peel seam. Likewise, the dividing line 509b preferably consists of a peel seam. In the preferred embodiment illustrated here the peel seams of the dividing line of 509 and 509b form an integral construction of peel seam sections which develop into one another so that an incipient peel seam break of the dividing line of 509 is also propagated to dividing line 509b.

A port 506 connects the inside of the bag via a first end in the inside of the bag 506b and another end 506a outside of the bag 501. Port 506 is preferably attached in a fluid-tight manner by weld connections in the circumferential dividing line 508. Means 506c for generating fluid turbulence in the inflowing diluent are preferably provided on the end 506b of the port 506. These means may be designed as a turbulence-generating nozzle or as a turbulence-generating frit. Port 506 preferably consists of a tube which passes through the bag in the interior in its longitudinal extent. This ensures that in the filling method with the bag in an upright position, for example, by holding the bag on an integral holding rail 511, the bag is filled from the bottom and the concentrate chambers A, B, C are opened in the order B, A, C by the internal filling pressure.

By filling the bag 501 through the port 506 with diluent, the diluent flows into the filling chamber 510. With an increase in the degree of filling, a tensile stress acts on the dividing line 509, resulting in the dividing line 509 being partially released and the concentrate 504 being mixed with the diluent. With further filling, the concentrate chamber A is also opened by releasing the dividing line 509a so the concentrate 505 is mixed with the diluent and concentrate 504 that is already partially or fully dissolved. Concentrate 505 makes a contribution toward the electrical conductivity in solution. By further filling of the bag 501 the dividing line 509 and the dividing line 509b are dissolved completely so that the concentrates are mixed with the diluent. The quantities of solution components and diluents are such that a finished physiologically acceptable solution, in particular dialysis solution is formed. Through changes in conductivity, which are attributable to dissolving or dilution of the concentrates in concentrate chamber A during the process of preparation of the medicinal solution, it is possible to ensure that circumferential line 509 has been broken open and the chamber contents B which do not contribute toward the conductivity of the solution to be prepared, are released and dissolved.

Another port 507 having a first end 507a outside of the bag and another end 507b inside of the bag serves to remove or supply solution, substances, medications, etc.

Figure 6:
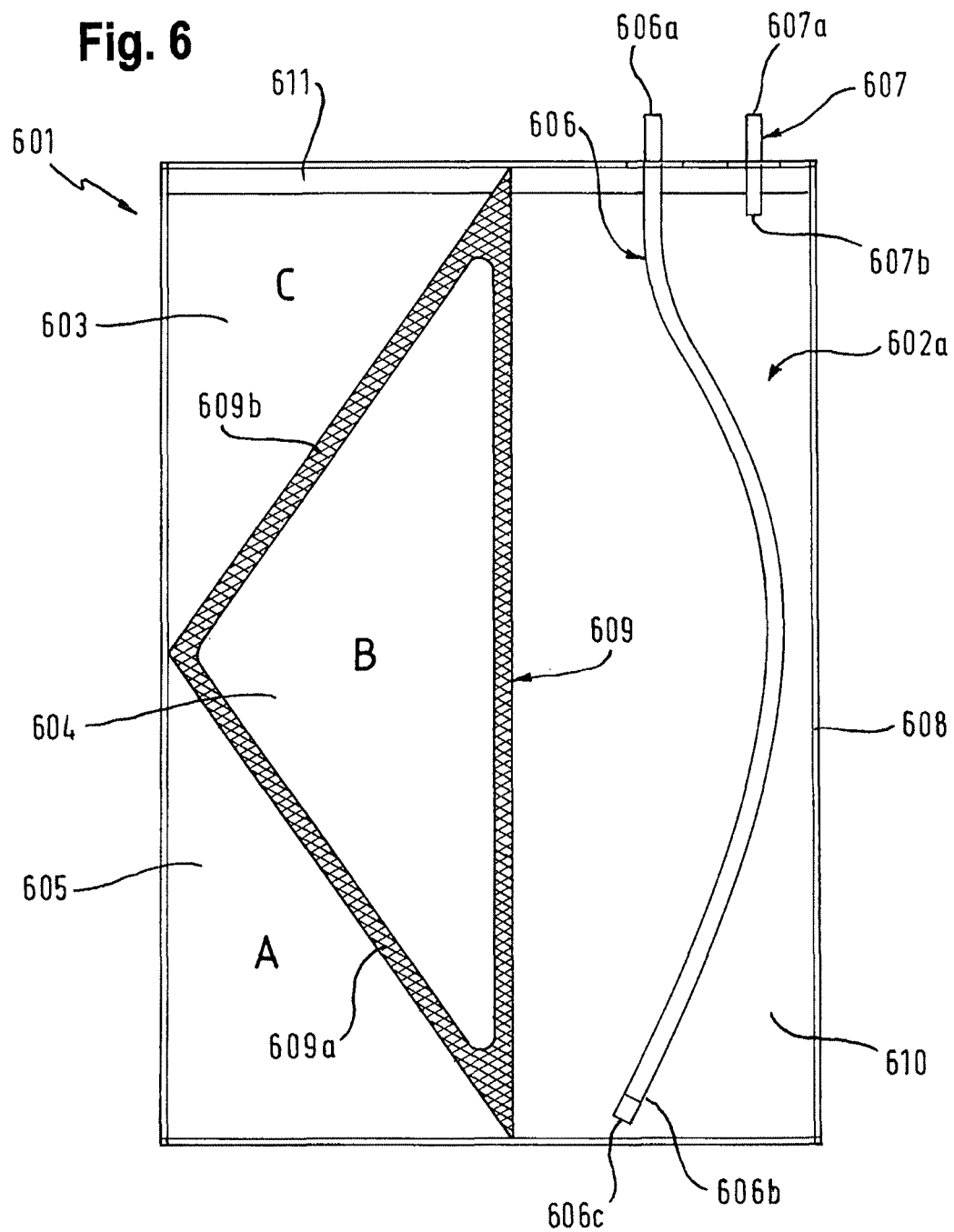
FIG. 6 shows another inventive container having three chambers containing solution components.

FIG. 6 shows another embodiment. The container 601, preferably the bag, has an upper outside wall 602a in the perspective of FIG. 6 and a lower outside wall 602b (not shown) which are bordered by a shared circumferential edge 608 and are connected in a fluid-tight manner. In a preferred version 602a and 602b are the upper and lower film sheets of a bag. The bag also consists of the concentrate chambers A, B, C with concentrates 605, 604, 603. The concentrate 605 in concentrate chamber A according to Table 1 may be identical to the concentrates 5, 205a, 205b of the preceding embodiments 1, 201 and may make a minor contribution toward the electrical conductivity of the solution.

A port 606 connects the interior 610 of the bag via a first end in the filling chamber 610 of the bag and another end 606a outside of the bag 601 to the exterior of the bag. Port 606 is preferably attached in a fluid-tight manner in the circumferential dividing line 608 which is preferably a permanent weld. Means 606c for generating fluid turbulence in the inflowing diluent are preferably provided at the end 606b of the port 606. These means may be designed as a turbulence-generating nozzle or as a turbulence-generating frit. Port 606 preferably consists of a tube which passes through the bag in the interior in its longitudinal extent. Thus it is ensured in the filling process that when the bag is held upright, for example, by accommodating the bag on an integral holding rail 611, the bag is filled from the bottom and the concentrate chambers A, B, C are opened by the internal filling pressure in the order B, A, C or A, B, C.

The chambers A, B, C are surrounded by a circumferential line 609, which is formed in sections from a part of the bag circumferential line 608 of the bag and another part of a dividing line which has at least partially semipermanent sections. The first dividing line of the circumferential line 609 preferably consists of a peel seam and borders two concentrate chambers in a section 612. This ensures that a peelable section can release two concentrates in dissolving the peel seam. The contents of the concentrate chambers A, B, C are separated from one another by additional dividing lines 609a, 609b. The additional dividing line 609a is semipermanent in at least some sections and is preferably a completely semipermanent weld line, for example, a peel seam. In the one preferred embodiment shown here the peel seams of the dividing lines of 609, 609a, 609b form an integral construction of peel seam sections which develop into one another so that an incipient peel seam break of the dividing line of 609 is also continued to the dividing line 609a and 609b.

The concentrate 604 in concentrate chamber B may be identical according to Table 1 to the concentrates 4, 204a, 204b of the preceding embodiments 1, 201 and may not make any contribution toward the electrical conductivity of the solution.

The concentrate 603 in concentrate chamber C may be identical according to the table to the solution components 3, 203a, 203b of the preceding embodiments 1, 201 and may make a contribution toward the electrical conductivity of the solution.

By filling the bag 601 through the port 606 with diluent, the diluent flows into a filling chamber 610. With an increase in the degree of filling a tensile stress acts on the dividing line 609, resulting in partial dissolution of the dividing line 609, so the concentrates 604 and/or concentrate 605 at the same time become mixed with the diluent. With further filling, the concentrate chamber A also opens by dissolving of the dividing line 609a, unless it is opened simultaneously with chamber B according to the embodiment shown. Concentrate 605 preferably consists of substances which make a minor contribution to the electrical conductivity of the solution. By further filling of the bag 601 the dividing line of 609 is dissolved and then the dividing line 609a, 609b is dissolved completely so that the concentrate 603 becomes mixed with the diluent and concentrates 605 and 604. The quantities of concentrates and diluents are such that a finished physiologically acceptable solution, in a particular dialysis solution, is formed.

Another port 607 with a first end 607a outside of the bag and another end 607b inside the bag serves to remove or supply solution, substances, medications, etc.

Figure 7:
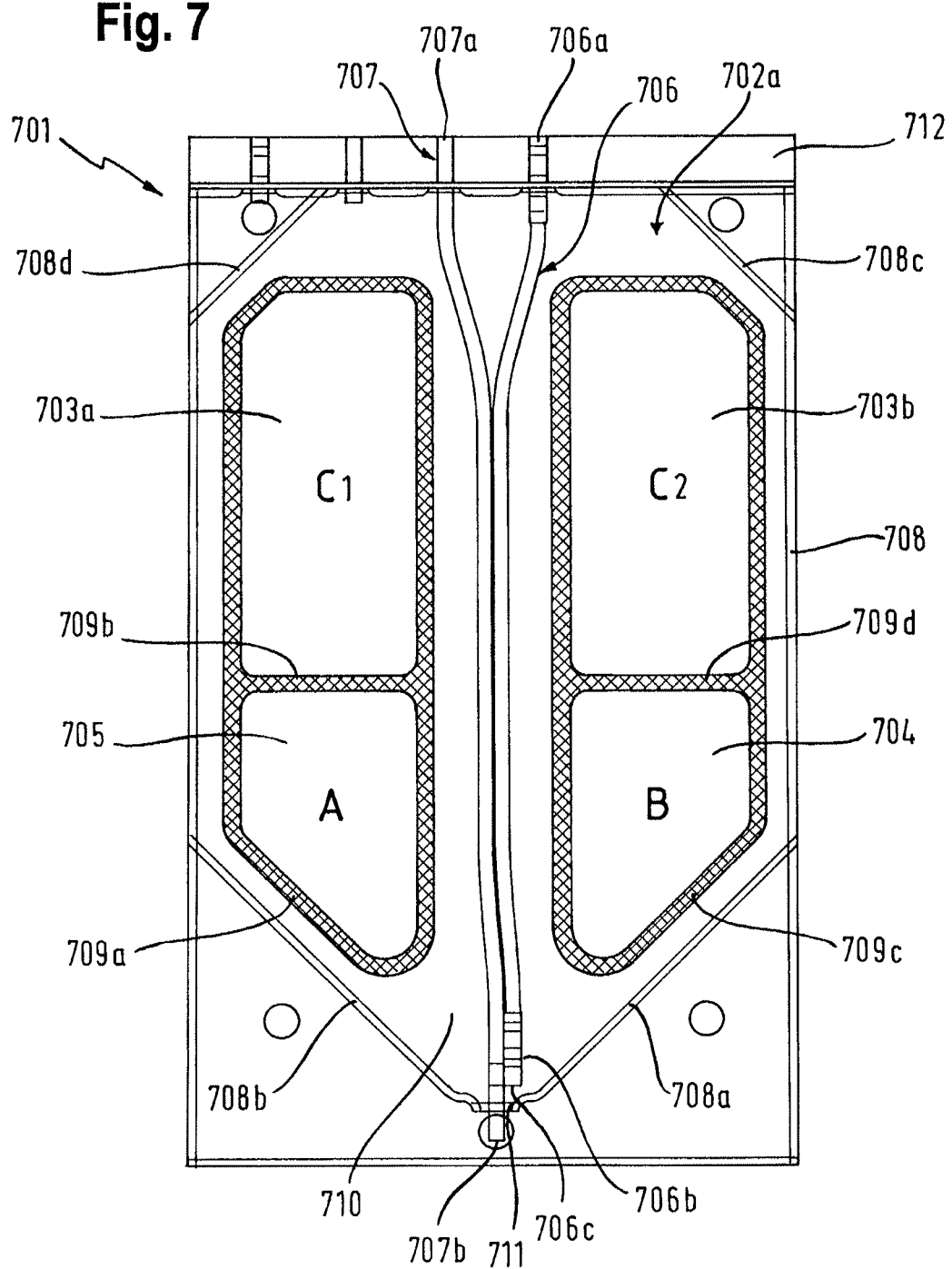
FIG. 7 shows an inventive container having four chambers.

FIG. 7 shows another embodiment which is like the embodiment according to FIG. 2. The container has in perspective to the plane of the drawing an upper outside wall 702a and a lower outside wall 702b (not shown) which are bordered by a shared circumferential edge 708 and are connected in a fluid-tight manner. In a preferred version, 702 and 702b are the upper and lower film sheets of a bag, and 708 is formed by a permanent weld.

The bag has a first concentrate chamber A with concentrates 705, which in one exemplary embodiment consist of substances which make a contribution toward the electricity conductivity in solution. According to the exemplary embodiments in Table 1, the concentrate chamber A contains the concentrate 705, the substances magnesium carbonate or in general soluble magnesium salts, calcium salts, for example, dissolved or in solid form, magnesium chloride and/or calcium chloride, citric acid or citrate salts, acid salts or acids in solid or dissolved form.

A second concentrate chamber C1 with concentrate 703a contains in one exemplary embodiment substances which make a contribution toward the electricity conductivity in solution. In one exemplary embodiment this may be sodium chloride and/or bicarbonate or in general soluble salts of carbonic acid, for example, sodium carbonate or other physiologically tolerable buffers, for example, salts of weak acids.

The concentrate chambers A and C1 are enclosed by a dividing line 709a along a closed circumferential line, consisting of a semipermanent dividing line in at least some sections in the embodiment shown here. In one embodiment the first dividing line 709a consists of a peel seam. The contents of the concentrate chambers A and C1 are separated from one another by the additional dividing line 709b. The additional dividing line 709b may consist of a permanent weld line, a partially semipermanent weld line or a peel seam. The dividing lines 709a and 709b are preferably designed as peel seams and form a cohesive integral construction of peel seam sections.

The exemplary embodiment according to FIG. 7 is also characterized in that a connecting port 706 connects the filling chamber 710 of the bag to the outside of the bag via a first end in the interior of the bag 706b and another end 706a outside of the bag 701. Port 706 is preferably attached by welded joints in the circumferential dividing line 708 in a fluid-tight manner. Means 706c for generating fluid turbulence in the inflowing diluent are preferably provided at the end 706b of the port 706. These means may be designed as a fluid-generating nozzle or as a turbulence-generating frit. In addition, the port 706 consists of a tube which passes through the bag in the interior in its longitudinal extent. This ensures that in the filling method with upright storage of the bag, for example, by accommodating the bag on an upper holding rail 712, the bag is filled from beneath and the concentrate chambers A, B, C1, C2 are opened by the internal filling pressure in the order A simultaneously with B before C1 simultaneously with C2.

Another port 707 with a first end 707a outside of the bag and another end 707b serves to return spent medical fluid, preferably dialysis solution. Port 707 is designed as a tube in the interior of the bag and is provided for passing through the bag along a longitudinal extent when the bag is stored in a hanging position, for example, by accommodating the bag on the upper holding rail 712. At the location 711 the tube 707 passes through the circumferential line 708 on the bag 701 and opens into another chamber (not shown). The location 711 may be a fluid sealing weld which secures the bag between the upper and lower bordering planes 702a and 702b and is part of the welded circumferential line 708. The chamber (not shown) may be a sheathing container, preferably a bag, which may be an integral component of the container 701. Thus this yields a "bag in bag" construction in which the bag which holds the ready-to-use liquid is enclosed by a bag holding the spent fluid. Likewise, the chamber (not shown) may also be designed to be separation.

In addition, the embodiment in FIG. 7 shows a second set of concentrate chambers B, C2 which are surrounded by another dividing line along a closed circumferential line 709c. Another dividing line 709d separates the contents of the concentrate chambers B and C2. In a preferred embodiment the peel seams 709c and 709d form an integral construction of peel seam sections which develop into one another.

In the exemplary embodiment, the concentrate 704 in chamber B consists of substances which do not make any contribution toward the electrical conductivity in solution. In an exemplary embodiment according to Table 1, it may be anhydrous glucose.

The concentrate 705 and the concentrate chamber A in the embodiment from FIG. 2 may be identical or may contain only some of the components 205a. In an exemplary embodiment, the concentrate 705 consists of magnesium carbonate or in general soluble magnesium salts, calcium chloride or soluble potassium salts, citric acid or citrate salts in general or another acid.

Another concentrate chamber C2 with concentrate 703b contains additional substances which are incompatible with the substances of concentrates 705, 704, i.e., tend to degradation or unwanted interactions. In addition, concentrate 703b in solution makes a contribution toward the electrical conductivity. This ensures that with an increase in the electrical conductivity due to dissolving of the components 703b, the dissolving of components 704 also takes place because the solution components in chambers B and C2 are bordered and separated by a cohesive peel seam system that is to be opened.

This embodiment also shows a circumferential line 708 consisting preferably of a permanent weld. Additional permanent weld lines, sections 708a and 708b border the container contents or bag contents in such a way as to form an oblique bottom of the interior space. This design facilitates turbulence in the inflowing diluent caused by means 706c which generate fluid turbulence and thus facilitate the dissolving process of the components 705, 704, 703a, 703b. Bordering lines 708c and 708d impart additional stability to the filled container, in particular bag in the filled state. This is important in particular for large-volume containers in which the internal pressure due to the quantities contained in the bag can exert a loading stress effect on the circumferential line 708. Large-volume bags in this sense are to be understood as containers having a volume of 5 to 120 liters, 40 to 80 liters, in particular 60 liters±15%.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. A container suitable for preparing medicinal solutions consisting of permanent outside walls which define an internal capacity of the container, comprising
    a filling chamber, a first concentrate chamber and a second concentrate chamber which are arranged in an interior of the container,
    the first and second concentrate chambers being separated by dividing lines which are semipermanent in at least some sections,
    including a first dividing line, which separates the filling chamber from the first concentrate chamber and the second concentrate chamber, and surrounds the first concentrate chamber and the second concentrate chamber along a closed line, without cooperating with a circumferential line of the container.

2. The container according to claim 1, wherein the filling chamber includes a feed port of the container.

3. The container according to claim 1, wherein the filling chamber is empty.

4. The container according to claim 1, further comprising at least one of a third concentrate chamber, a fourth concentrate chamber, a fifth concentrate chamber, a sixth concentrate chamber, a seventh concentrate chamber, and an eighth concentrate chamber.

5. The container according to claim 1, further comprising a third concentrate chamber, and wherein the first dividing line surrounds the first concentrate chamber, the second concentrate chamber and the third concentrate chamber.

6. The container according to claim 1, wherein the container is a bag.

7. The container according to claim 1, wherein the first dividing configured as a peel seam in at least some sections thereof.

8. The container according to claim 1, wherein the first dividing line is uniformly a peel seam.

9. The container according to claim 7, wherein the peel seam has a strength of from 0.1 to 8 N/15 mm.

10. The container according to claim 1, wherein the dividing line that separates the first concentrate chamber and the second concentrate chamber is a second dividing line.

11. The container according to claim 10, wherein the first dividing line and the second dividing line are configured as an integral peel seam construction.

12. The container according to claim 5, wherein the first concentrate chamber and the third concentrate chamber are separated from one another by a third dividing line.

13. The container according to claim 10, the one first dividing line, further comprising a third concentrate chamber separated from the first concentrate chamber by a third dividing line, and wherein the second dividing line and the third dividing line are configured as an integral peel seam construction.

14. The container according to claim 6, wherein the container has a material of construction that is an elastically extensible film material.

15. The container according to claim 1, wherein the first concentrate chamber contains a concentrate (B) which does not make any significant contribution toward an electrical conductivity in solution.

16. The container according to claim 15, wherein the concentrate (B) includes glucose.

17. The container according to claim 1, wherein the second concentrate chamber contains a concentrate (C, C1, C2) which makes a contribution toward an electrical conductivity in solution.

18. The container according to claim 17, wherein ions selected from the group consisting of sodium, magnesium, calcium, potassium, carbonate, bicarbonate, acetate, lactate, and chloride are dissolved with a release of the concentrate (C, $C_1$, $C_2$) of the second concentrate chamber.

19. A method of preparing a medicinal solution from multiple concentrates (A, B, $B_1$, $B_2$, C, $C_1$, $C_2$) associated with a container according to claim 1, said method comprising the steps of:
    introducing a liquid into a filling chamber of the container;
    breaking up in a semipermanent dividing line which borders the first concentrate chamber due to developing hydrostatic pressure;
    releasing the concentrates (A, B, $B_1$, $B_2$) which make essentially no contribution toward an electrical conductivity of the medicinal solution;
    additional filling and application of pressure and breaking open of the dividing line or another dividing line which borders another concentrate chamber at a same time or with a time offset; and
    releasing the concentrate (C, $C_1$, $C_2$) of one additional concentrate chamber which makes a contribution toward the electrical conductivity of the solution.

20. The method according to claim 19, wherein the preparing of the solution is monitored by measuring the conductivity thereof.

* * * * *